United States Patent
Glusker et al.

(10) Patent No.: US 10,258,752 B2
(45) Date of Patent: Apr. 16, 2019

(54) BLISTER TRACK INHALER DEVICE HAVING A SEPARATE END PATH AND METHODS OF USE THEREOF

(71) Applicants: Mark Glusker, San Mateo, CA (US); Victoria Quitugua, Palo Alto, CA (US)

(72) Inventors: Mark Glusker, San Mateo, CA (US); Victoria Quitugua, Palo Alto, CA (US)

(73) Assignee: Novartis AG, Basel (CH)

( * ) Notice: Subject to any disclaimer, the term of this patent is extended or adjusted under 35 U.S.C. 154(b) by 269 days.

(21) Appl. No.: 14/495,928

(22) Filed: Sep. 25, 2014

(65) Prior Publication Data

US 2015/0090262 A1 Apr. 2, 2015

Related U.S. Application Data

(60) Provisional application No. 61/885,276, filed on Oct. 1, 2013.

(51) Int. Cl.
*A61M 15/00* (2006.01)

(52) U.S. Cl.
CPC .... *A61M 15/0051* (2014.02); *A61M 15/0025* (2014.02); *A61M 15/0026* (2014.02); *A61M 15/0036* (2014.02); *A61M 15/0041* (2014.02); *A61M 15/0055* (2014.02); *A61M 15/0068* (2014.02); *A61M 2202/064* (2013.01); *A61M 2205/58* (2013.01)

(58) Field of Classification Search
CPC ..................... A61M 2202/064; A61M 2205/58
See application file for complete search history.

(56) References Cited

U.S. PATENT DOCUMENTS

| | | | |
|---|---|---|---|
| 6,557,550 B1 * | 5/2003 | Clarke | A61M 15/0065 128/203.15 |
| 6,725,857 B2 | 4/2004 | Ritsche | |
| 7,878,196 B2 | 2/2011 | Pocock et al. | |
| 8,087,411 B2 | 1/2012 | Pocock et al. | |

(Continued)

FOREIGN PATENT DOCUMENTS

| | | |
|---|---|---|
| EP | 2077132 A1 | 7/2009 |
| EP | 2082761 A1 | 7/2009 |

(Continued)

*Primary Examiner* — Gregory Anderson
*Assistant Examiner* — Jonathan Paciorek
(74) *Attorney, Agent, or Firm* — Michael J. Mazza

(57) ABSTRACT

Embodiments of an inhaler device include a housing, a withdrawing assembly disposed within the housing for facilitating withdrawal of medicament from a target blister of a blister strip, the withdrawing assembly including an opening element adapted for opening the target blister of the blister strip while the target blister is positioned in the withdrawing assembly, and a dispensing element adapted for directing the withdrawn medicament toward the exterior of the inhaler device. A blister track is disposed within the housing for guiding each blister of the blister strip to the withdrawing assembly in succession, an advancing mechanism for advancing the blister strip by a predetermined distance each time the advancing mechanism is engaged, and an engaging element for engaging the advancing mechanism to advance the blister strip. The blister track includes a primary coil structure, a secondary coil structure, and a tertiary coil structure.

9 Claims, 9 Drawing Sheets

(56) References Cited

U.S. PATENT DOCUMENTS

| | | |
|---|---|---|
| 8,671,939 B2 | 3/2014 | Kirniak |
| 8,746,243 B2 | 6/2014 | Kirniak |
| 2006/0196504 A1* | 9/2006 | Augustyn ......... A61M 15/0045 128/203.15 |
| 2008/0099016 A1 | 5/2008 | Pocock et al. |
| 2009/0007908 A1* | 1/2009 | Eason ............... A61M 15/0045 128/203.15 |
| 2009/0314291 A1* | 12/2009 | Anderson ......... A61M 15/0045 128/203.15 |
| 2010/0012119 A1 | 1/2010 | Sallak et al. |
| 2010/0139654 A1* | 6/2010 | Thoemmes ....... A61M 15/0045 128/203.15 |
| 2010/0229856 A1* | 9/2010 | Von Brunn ....... A61M 15/0045 128/200.23 |
| 2010/0288278 A1 | 11/2010 | Pocock et al. |
| 2011/0114088 A1 | 5/2011 | Eason et al. |
| 2011/0297151 A1 | 12/2011 | Jung |

FOREIGN PATENT DOCUMENTS

| | | |
|---|---|---|
| GB | 2407042 A | 4/2005 |
| WO | 90/13328 A1 | 11/1990 |
| WO | 92/08509 A1 | 5/1992 |
| WO | 94/27653 A2 | 12/1994 |
| WO | 96/06581 A1 | 3/1996 |
| WO | 2003/035508 A1 | 5/2003 |
| WO | 2003/090811 A2 | 11/2003 |
| WO | 2003/090825 A1 | 11/2003 |
| WO | 2004/011067 A1 | 2/2004 |
| WO | 2009/092769 A1 | 7/2009 |
| WO | 2009/092770 A1 | 7/2009 |
| WO | 2012012827 A1 | 2/2012 |

* cited by examiner

BLISTER TRACK INHALER DEVICE HAVING A SEPARATE END PATH AND METHODS OF USE THEREOF

FIELD OF THE INVENTION

The present invention relates to an inhaler device for pulmonary delivery of medicaments, and particularly to an inhaler device that utilizes a blister strip that includes a plurality of blisters containing a powdered medicament.

BACKGROUND

It is often desirable or convenient to deliver a medicament to a patient pulmonarily, using a dispensing device, such as an inhaler device (or simply, an "inhaler"). The inhaler device may be adapted to dispense a product, for example a medicament dose, from blisters within which a discrete dose of a medicament is stored. This is particularly the case for inhalers where the medicament is typically in a powdered form to be inhaled by a patient. Conventionally, blister-based unit dose inhalers use blister packs having only a single blister cavity which may be inserted, opened, and the medicament inhaled therefrom. However, such single dose inhalers may not be convenient for all patients since additional individual blisters must be carried with the inhaler device any time a patient will need to use multiple doses over a period of time. Additionally, unit dose inhalers require the patient to locate, manipulate, insert and remove the blister each time a medicament dose is desired.

Accordingly, multiple dose inhalers that use a blister strip have been developed. In such inhalers, the blister strip has a plurality of blisters thereon and the strip is moved (longitudinally or rotationally) so that blisters are sequentially presented to a dispensing position from which the medicament may be dispensed to the patient, such as during inhalation. The blisters are opened when they are positioned in the dispensing position, or as they are moved to the dispensing position.

Some medicaments or inhalers may use blisters that are comparatively large, and in such cases, arranging the blisters in blister strips may result in a device which is unacceptably large, inconveniently shaped, overly cumbersome to use, and/or contain too few doses of medicament to be widely accepted by patients.

In some inhaler devices, as blisters exit the inhaler device on the blister strip, the blisters must be removed and/or disposed of by cutting or tearing the blister strip, which is not considered a preferred patient use scenario. This is because the used blisters on the blister strip may hinder operation of the device, or may become a hindrance as they accumulate along with the device, or may disperse remaining medicament to locations exterior of the inhaler device, etc., any of which are not acceptable to patients.

In other inhaler devices, a single or dual take-up reel may be used to coil up used blisters in the interior of the inhaler device. However, these inhaler devices must be larger to account for the additional space necessary to house the used blisters.

In addition, since inhaler devices may be used by patients of all ages, strengths, and capabilities, it is useful that the inhaler device provide uniform and easy operation from the first blister to the last, including installation and removal of blister strips from the inhaler device. Some older and/or frailer patients may not have the requisite strength to operate an inhaler device in some operating conditions that a younger or stronger patient may be able to operate. However, each of these patients, irrespective of relative physical attributes (that is over a range of physical attributes) should be able to operate the inhaler device with equal ability regardless of the blister strip position in the inhaler device.

SUMMARY

Accordingly, one embodiment of the invention comprises an inhaler device comprising a housing, a withdrawing assembly disposed at least partially within the housing being adapted for facilitating withdrawal of medicament from a target blister of a blister strip and conveying the medicament toward an exterior of the inhaler device, a blister track disposed within the housing, the blister track being adapted for guiding each blister of the blister strip to the withdrawing assembly in succession and storing the blister strip prior to, during, and after use of blisters of the blister strip, an advancing mechanism disposed within the housing, the advancing mechanism being adapted for advancing the blister strip by a predetermined distance each time the advancing mechanism is engaged, and an engaging element adapted for engaging the advancing mechanism to advance the blister strip, the engaging element being operable by the user.

The withdrawing assembly includes an opening element adapted for opening the target blister of the blister strip while the target blister is positioned in the withdrawing assembly, wherein the opening element is operable by a user, and a dispensing element adapted for directing the withdrawn medicament toward the exterior of the inhaler device.

In some embodiments, the blister track comprises a primary coil structure having a first radius, a secondary coil structure having a second radius, a third radius, and a fifth radius, and a tertiary coil structure having the second radius, a fourth radius, and the fifth radius.

In some embodiments of the present invention, an inhaler device comprises a housing; a withdrawing assembly disposed at least partially within the housing, the withdrawing assembly being adapted for facilitating withdrawal of medicament from a target blister of a blister strip and conveying the medicament toward an exterior of the inhaler device, wherein the withdrawing assembly comprises an opening element adapted for opening the target blister of the blister strip while the target blister is positioned in the withdrawing assembly, wherein the opening element is operable by a user; and a dispensing element adapted for directing the withdrawn medicament toward the exterior of the inhaler device; a blister track disposed within the housing, the blister track being adapted for guiding each blister of the blister strip to the withdrawing assembly in succession and storing the blister strip prior to, during, and after use of blisters of the blister strip, wherein the blister track comprises a primary coil structure comprising a first radius, a secondary coil structure comprising a second radius, a third radius, and a fifth radius, and a tertiary coil structure comprising the second radius, a fourth radius, and the fifth radius; an advancing mechanism disposed within the housing, the advancing mechanism being adapted for advancing the blister strip by a predetermined distance each time the advancing mechanism is engaged; and an engaging element adapted for engaging the advancing mechanism to advance the blister strip, the engaging element being operable by the user.

In some embodiments of the present invention, an inhaler device comprises a housing; a withdrawing assembly disposed at least partially within the housing, the withdrawing assembly being adapted for facilitating withdrawal of a medicament from a target blister of a blister strip and conveying the medicament toward an exterior of the inhaler device; and a blister advancing mechanism disposed within the housing and adapted for advancing the blister strip from an initial position where a leading edge of the blister strip is positioned in a primary coil, to a final position where the leading edge of the blister strip is positioned in a secondary coil, wherein at least the leading edge of the blister strip passes through the starting position of a trailing edge of the blister strip along the primary coil when the blister strip is advanced from the initial position to the final position.

In some embodiments of the present invention, an inhaler device comprises a blister track path and blister advance mechanism configured for providing a substantially consistent resistance to movement of the blister strip therethrough.

In some embodiments of the present invention, an inhaler device comprises a blister track path and blister advance mechanism configured to provide to a user an approximately equal amount of resistance to operation of the engaging element regardless of which blister of the blister strip is positioned as the target blister.

In some embodiments of the present invention, an inhaler device comprises, a blister track path and blister advance mechanism wherein an amount of resistance to operation of the engaging element for advancing the blister strip past a first blister is about equal to an amount of resistance to operation of the engaging element for advancing the blister strip past a final blister.

Other aspects and embodiments of the present invention will become apparent from the following detailed description, which, when taken in conjunction with the drawings, illustrate by way of example the principles of the invention.

DETAILED DESCRIPTION

Figure 1:
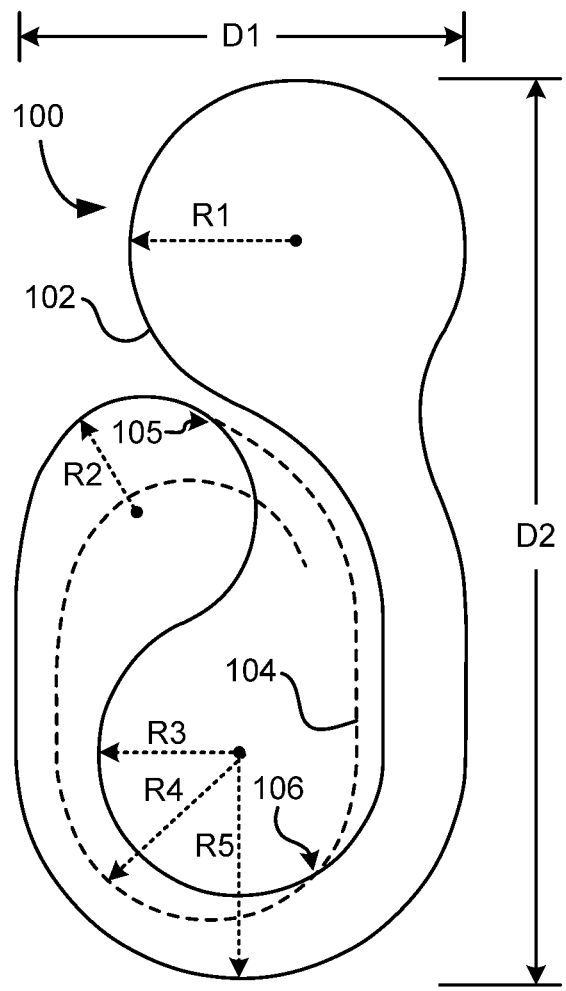
FIG. 1 shows a simplified diagram of an inhaler device with a separate end path, according to one embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a", "an", and "the" include plural unless otherwise specified.

According to one general embodiment, an inhaler device comprises a housing, a withdrawing assembly disposed at least partially within the housing being adapted for facilitating withdrawal of medicament from a target blister of a blister strip and conveying the medicament toward an exterior of the inhaler device, a blister track disposed within the housing, the blister track being adapted for guiding each blister of the blister strip to the withdrawing assembly in succession and storing the blister strip prior to, during, and after use of blisters of the blister strip, an advancing mechanism disposed within the housing, the advancing mechanism being a blister advancing mechanism adapted for advancing the blister strip by a predetermined distance each time the advancing mechanism is engaged, and an engaging element adapted for engaging the advancing mechanism to advance the blister strip, the engaging element being operable by the user.

In some embodiments, the withdrawing assembly includes an opening element adapted for opening the target blister of the blister strip while the target blister is positioned in the withdrawing assembly, wherein the opening element is operable by a user, and a dispensing element adapted for directing the withdrawn medicament toward the exterior of the inhaler device. The blister track comprises a primary coil structure having a first radius, a secondary coil structure having a second radius, a third radius, and a fifth radius, and a tertiary coil structure having the second radius, a fourth radius, and the fifth radius. It may be noted that the term "track" is generally used to refer to the blister strip guiding structure in its entirety, while the term "coil" is generally used to refer to a subset structure of the track, however, a coil structure may also be referred to sometimes as a "track," and vice versa.

In some embodiments, a multi-dose dry-powder inhaler comprises a housing, a withdrawing assembly comprising an opening element and a dispensing element, a blister track comprising multiple coil structures, an advancing mechanism, and an engaging element.

According to further embodiments, the multi-dose dry-powder inhaler may also comprise a blister track that minimizes one or more of the mean, maximum, and variability in torque experienced during blister strip advancement along the blister track. The size of the blister track remains relatively small compared to conventional blister tracks, and the overall device size may accordingly be relatively small compared to conventional multi-dose dry-powder inhaler devices. For example, in one embodiment the blister track may have dimensions of less than about 8.0 cm by about 4.5 cm by about 2.5 cm and the inhaler device may have overall dimensions of less than about 12.0 cm by about 7.5 cm by about 3.5 cm.

To minimize the space taken up by the blister strip during the course of the inhaler's useful life, the blister strip is kept within a blister track, in one embodiment. The blister strip is sequentially advanced one blister forward at a time along the blister track to access each dose of medicament stored within each blister.

Figure 5:
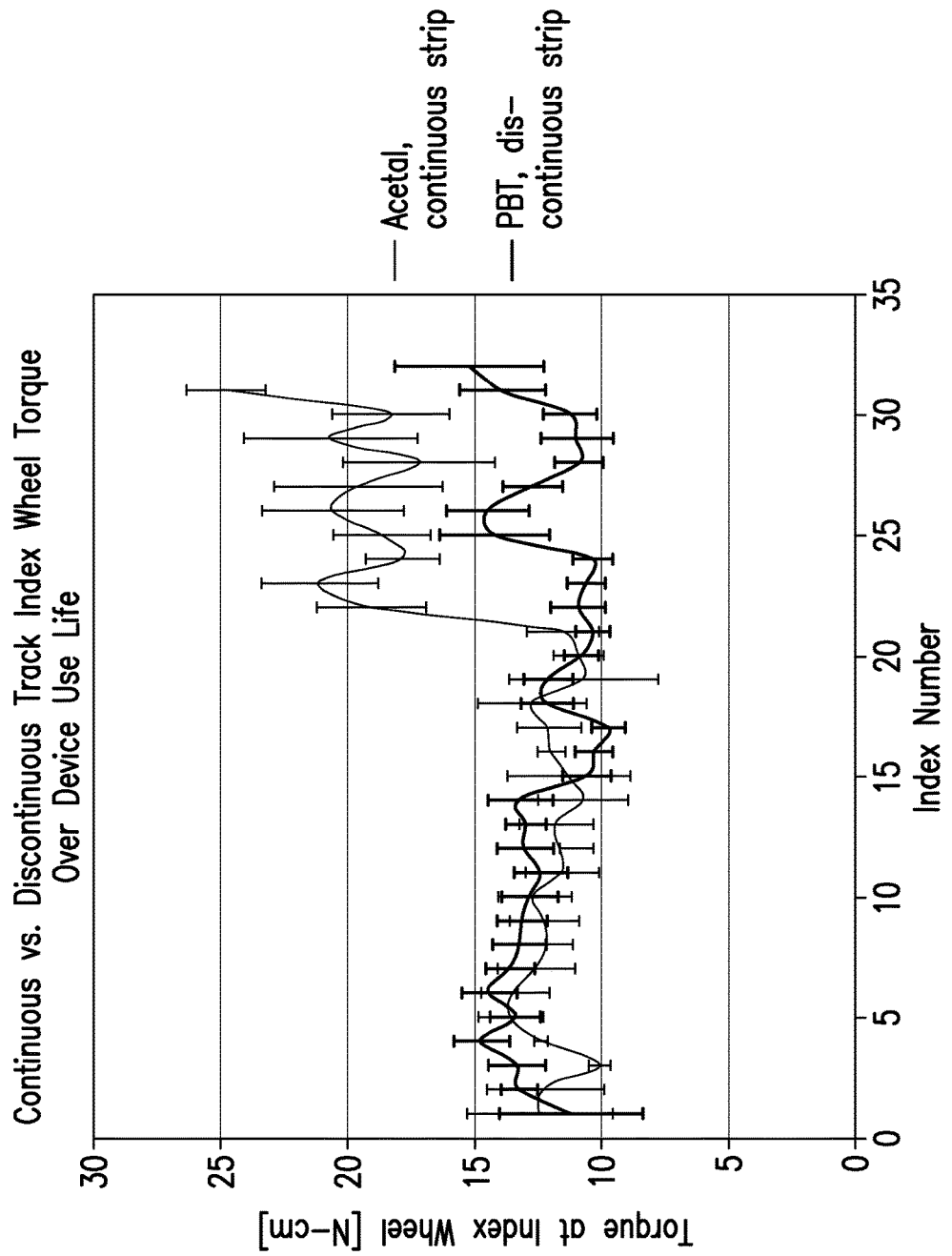
FIG. 5 is a graphical representation comparing advancing mechanism torque observed over the lifetime of an acetal-polymer inhaler device using a continuous blister track without a separate end path versus a PBT-polymer inhaler device using a blister track having a separate end path, according to one embodiment.

As shown in FIG. 1, in one embodiment the blister track may be arranged substantially as blister track 100 is arranged, that as, comprising a primary, secondary and tertiary coil structure. A discontinuous blister strip may be used in combination with the blister track 100 having a continuous path 102 and a separate low-torque end path 104, according to one embodiment and as shown in FIG. 1. Such arrangement of elements serves to reduce the peak torque experienced by the user during blister strip advancement. Notably, when the leading edge of the blister strip (which in the Figure, travels clockwise around the blister track 100) reaches the first junction 105, the blister strip may either enter the separate low-torque end path 104 or continue along the continuous path 102. However, less force is required to drive the blister strip into this low-torque end path 104 than to drive the blister strip further into the continuous path 102 of the blister track 100. Accordingly in embodiments of the invention, the blister strip is preferentially directed to the low-torque end path 104. Similarly, when the blister strip reaches the second junction 106, it may either continue along the low-torque end path 104 or return to the continuous path 102. Once again, in embodiments of the invention, the blister strip is directed to the low-torque end path 104. Ultimately, this requires less torque to be applied by a user to the advancing mechanism, as shown in the comparison of FIG. 5, according to some embodiments.

Furthermore, the overall size of the blister track 100 may be reduced such that the entire blister track 100 fits within an area defined by a width D1 and a length D2, according to various embodiments. Of course, there is also a depth which is not shown in the two dimensional rendering, but the blister track 100 may also be defined by this depth. In some embodiments, the blister track may have dimensions of a length D2 of less than about 8.0 cm by a width D1 of less than about 4.5 cm by a depth of less than about 2.5 cm. Of course, other dimensions are possible, as would be understood by one of skill in the art, such as about 7.9 cm×4.1 cm×2.2 cm, in one approach.

In addition to having a continuous path 102 and low-torque end path 104, various embodiments of the blister track 100 include three main coil structures defined by one or more radii of various turns in the blister track 100.

Figure 3A:
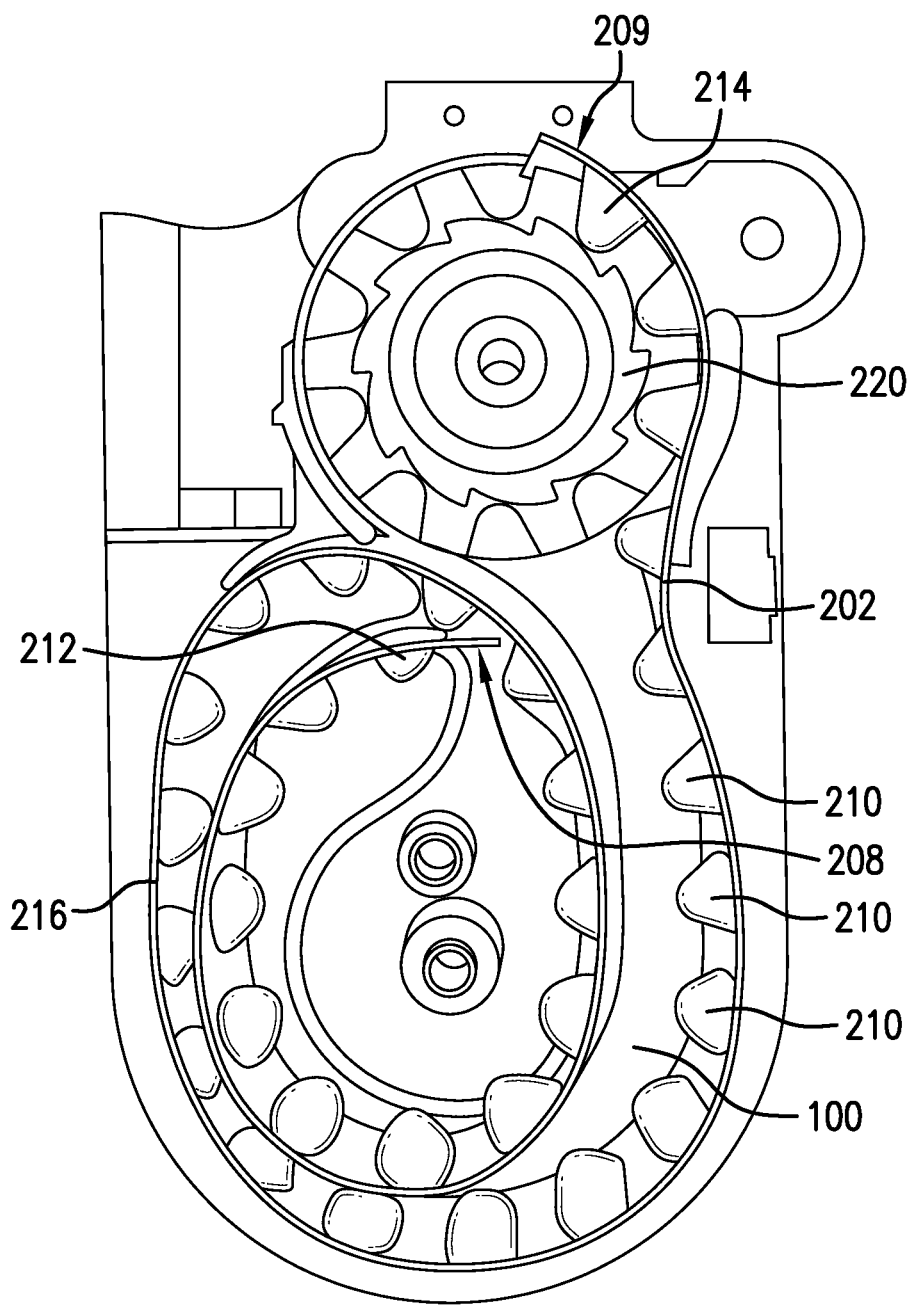
FIG. 3A is an image of an inhaler device with a separate end path loaded with a blister strip in a final position, according to one embodiment.
Figure 3B:
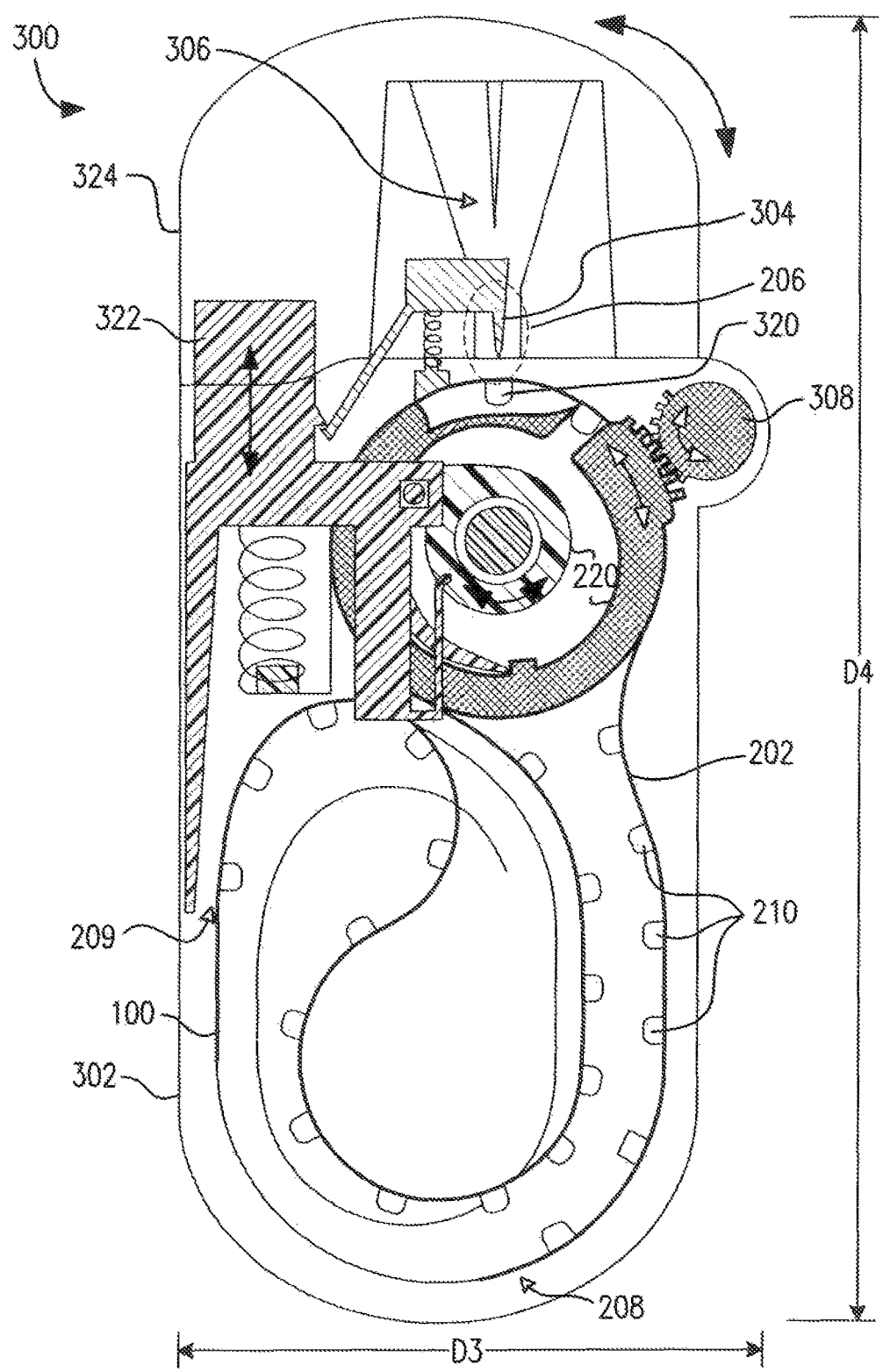
FIG. 3B is a detailed schematic of an inhaler device, according to one embodiment.
Figure 3C:
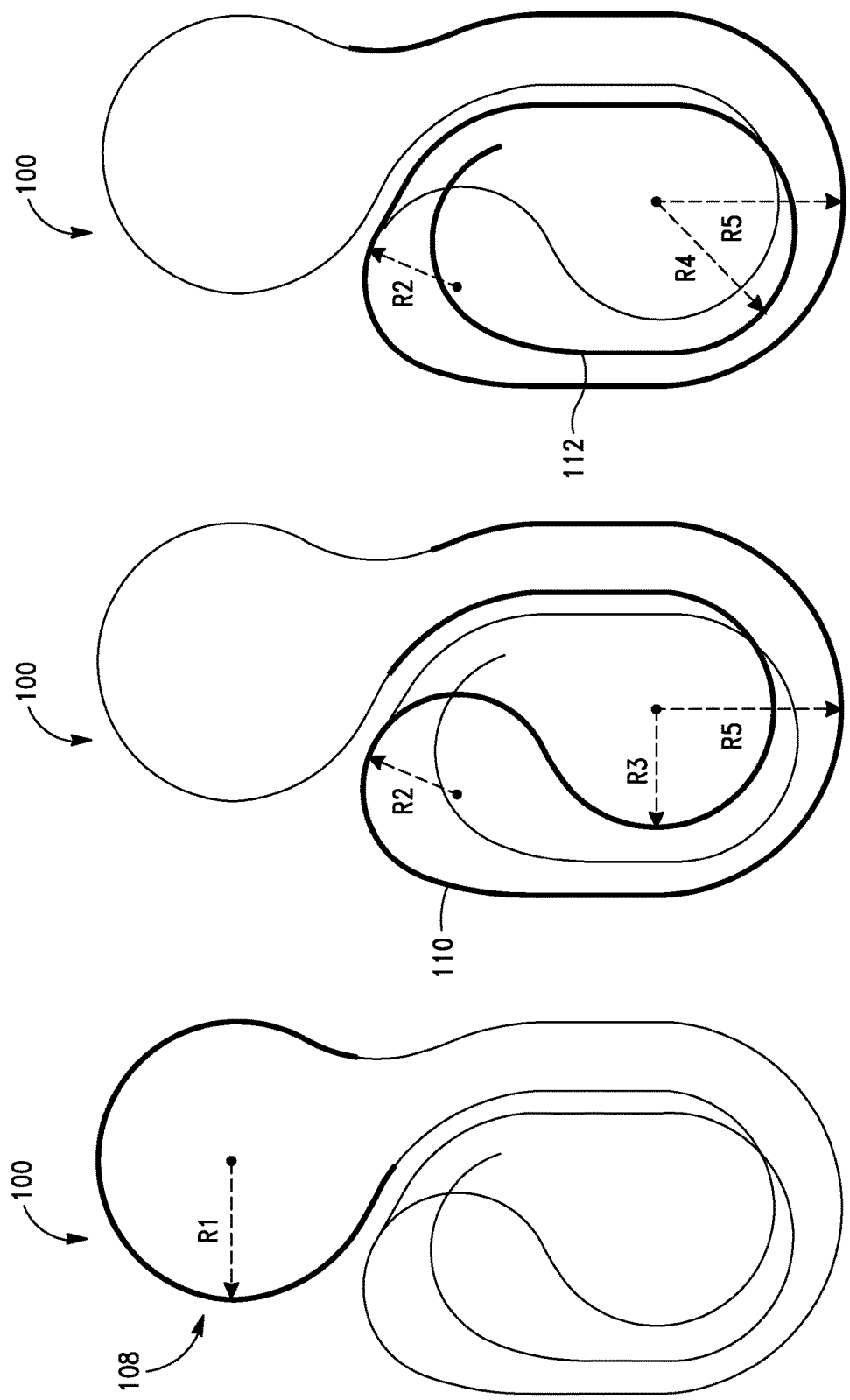
FIG. 3C shows schematics of coil structures of a blister strip of an inhaler device, according to several embodiments.

For example, as shown in FIG. 3C, the blister track 100 includes a primary coil structure 108 comprising a first radius R1, a secondary coil structure 110 comprising a second radius R2, a third radius R3, and a fifth radius R5, and a tertiary coil structure 112 comprising the second radius R2, a fourth radius R4, and the fifth radius R5. These respective radii may be further characterized by the relationships shown below in Equations 1-4, according to several embodiments.

$$R5 > R1 \quad \text{Eq. 1}$$

$$R1 > R4 \quad \text{Eq. 2}$$

$$R4 > R3 \quad \text{Eq. 3}$$

$$R3 \geq R2 \quad \text{Eq. 4}$$

In some embodiments, the respective arcs of the blister track 100 (shown in FIG. 1) have coinciding center points from which radii R3-R5 emanate. In some embodiments, the blister track 100 and/or coil structures are partially defined by radii of arcs that do not have coinciding center points, as would be appreciated by one having ordinary skill in the art upon reading the present descriptions.

In other words, the blister track 100 may be characterized in some embodiments as including a feeding path (which may include the secondary coil structure and a portion of the primary coil structure) adapted for storing the blister strip prior to blisters of the blister strip passing through the withdrawing assembly and a return path (which may include the tertiary coil structure and a portion of the primary coil structure) adapted for storing the blister strip after blisters of the blister strip have passed through the withdrawing assembly, where a portion of the feeding path is shared by a portion of the return path (such as at least the primary coil structure).

In addition, after the return path diverges from the feeding path, the return path allows used blisters on the blister strip to travel in a turn direction consistent with that of the feeding path immediately prior to a transition to the return path, e.g., if the feeding path wraps clockwise at this transition, the return path wraps clockwise, and vice versa. This aids in maintaining a low resistance to movement of the blister strip through and along the blister track 100.

Furthermore, in some embodiments of the present invention, a blister strip having used blisters thereon follows a different path (e.g., the return path) than a blister strip having unused blisters thereon (e.g., the feeding path). That is to say, in one approach, any given blister does not follow the same path on the blister track 100 twice.

Some embodiments of the blister track 100 have a geometry such that at the very end of the return path, the blister strip having used blisters thereon runs head on into another portion of the blister strip having used blisters thereon. Guidance of the beginning of the blister strip having used blisters thereon is provided by the motion of the other portion of the blister strip having used blisters thereon that it contacts, rather than being controlled by direct contact with the track walls of the blister track 100, in one approach. This geometry allows the blister strip to move the last few millimeters along the blister track 100 without increasing the overall size of the blister track 100, and keeps the resistance to movement low.

In some embodiments, the path of the blister track 100 may be configured to provide a substantially consistent resistance to movement of the blister strip therethrough. That is to say, the amount of resistance that the blister strip experiences as it moves through the blister track 100 is within about ±20% of a resistance value regardless of the position of the blister strip in the blister track 100. In some embodiments, the resistance value is a peak value or a nominal value or a predetermined datum value. In some embodiments, the resistance value tolerance is within about ±15% or ±12% or ±10% or ±8% of a resistance value.

According to some embodiments, the blister track 100 is configured to allow for a consistent torque profile while the advancing mechanism pulls blisters of the blister strip from the feeding path of the blister track 100 and pushes blisters of the blister strip toward and along the return path of the blister track 100. Preferably, this torque profile is lower than in conventional inhaler devices, such that a user experiences a low resistance to movement of the blister strip along the blister track 100.

In some embodiments, the user experiences about an equal amount of resistance to operation of the engaging element regardless of which blister of the blister strip is positioned as the target blister in the withdrawing assembly, hence the resistance to movement is generally consistent.

In some embodiments, the user experiences both a low and consistent amount of resistance to movement of the blister strip and/or engaging element.

In some embodiments, an amount of resistance to operation of the engaging element (described in more detail in reference to FIG. 3B) for advancing the blister strip past a first blister is about equal to an amount of resistance to operation of the engaging element for advancing the blister strip to a final blister.

Referring to FIG. 1, according to one embodiment the curvature of the arcs comprising radii R1, R2, R3, R4, and R5 may change uniformly or non-uniformly along the arcs, in some approaches. However, in some embodiments, the change in curvature of the blister track 100 is gradual.

Figure 2:
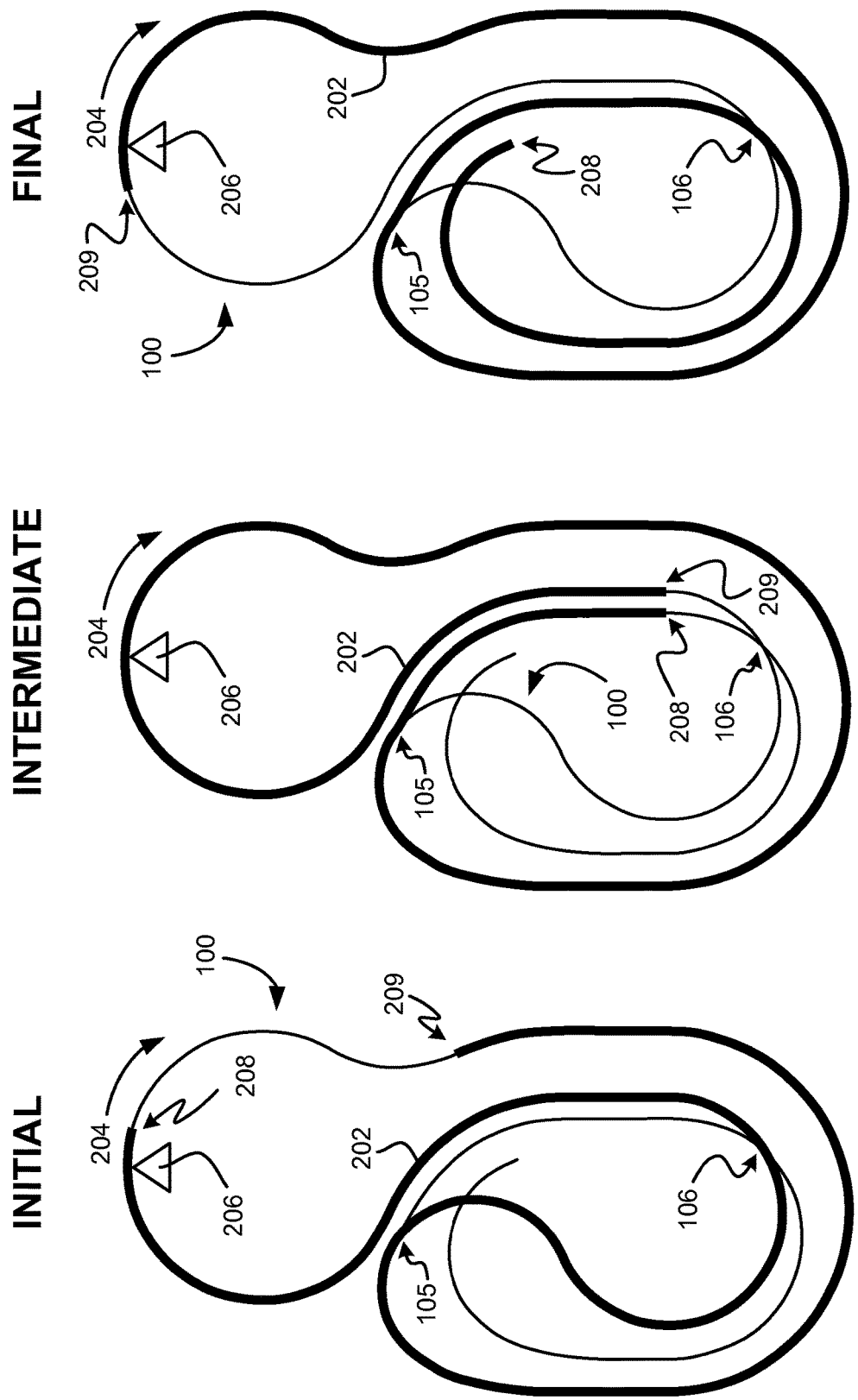
FIG. 2 shows schematics of a blister track with a separate end path of an inhaler device with a blister strip in various positions, according to several embodiments.

Referring now to FIG. 2, positions of an exemplary discontinuous blister strip 202 along a blister track 100 is shown at various stages of advancement of the blister strip 202, in some approaches. According to various embodiments, the discontinuous blister strip 202 may be characterized by a discrete leading edge 208 and trailing edge 209. Arrow 204 indicates direction of blister strip 202 travel, according to one embodiment.

As shown at the left of FIG. 2 and according to one embodiment, the blister strip 202 is placed in an initial position (shown in FIG. 2 as INITIAL) prior to the delivery of any medicament to a user or advancement of the blister strip 202. According to various embodiments, while in the initial position, the first blister in the blister strip 202 may be positioned in the withdrawing assembly 206 and the leading edge 208 of the blister strip 202 may be positioned just past the withdrawing assembly 206.

In one embodiment, this first blister may be a blank, e.g., it may contain no medicament. This allows a trained technician or automated process to operate the advancing mechanism of the inhaler device to position a blister which does not contain medicament into the withdrawing assembly 206 for performing release testing, e.g., measuring a pressure drop with a simulated inhalation, button push force (to pierce the target blister positioned in the withdrawing assembly 206), and/or cap closing force (to advance the blister strip) without contaminating the device with medicament powder.

In some embodiments, the inhaler device may be delivered to a user with the blank blister positioned in the withdrawing assembly 206 so that accidental discharge of the medicament will not take place (since the first blister contains no medicament).

As shown in FIG. 2, as the blister strip 202 sequentially places a first blister all the way to a last blister in the withdrawing assembly 206, the blister strip 202 advances through the blister track 100. The central portion of FIG. 2 shows the blister strip 202 in an intermediate position (shown in FIG. 2 as INTERMEDIATE) when a blister in-between the first blister and the last blister is positioned in the withdrawing assembly 206.

Now referring to the right-most portion of FIG. 2, the blister strip 202 is shown in a final position (shown in FIG. 2 as FINAL), where the final blister is positioned in the withdrawing assembly 206, and the leading edge 208 of the blister strip 202 is positioned in the tertiary coil structure, while the trailing edge 209 of the blister strip 202 is positioned just prior to the withdrawing assembly 206.

Of course, FIG. 2 shows examples of how the blister strip 202 may move through the blister track 100, according to one embodiment. Other configurations and arrangements are possible, as would be understood by one of skill in the art. However, the movement of the blister strip 202 through the blister track 100 as described has significant advantages over other configurations, including reduced torque requirement for movement of the blister strip 202 through the blister track 100, a more consistent torque profile (as is also evident from FIGS. 4A-4B), and reduced overall blister track 100 size, among other advantages.

Notably, as the blister strip 202 advances along the blister track 100, the portion of the blister strip 202 that has advanced beyond withdrawing assembly 206 is pushed along the blister track 100, while the portion of the blister strip 202 preceding the withdrawing assembly 206 is pulled along the blister track 100. This is an advantage over conventional inhaler devices, and in particular compared to inhaler devices which rely exclusively on either pushing or pulling forces to advance the blister strip 202 along its intended path (e.g., the blister track 100). For example, the inhaler device described herein according to various embodiments requires no additional leader or trailer on the blister strip 202 to engage the advancing mechanism. In embodiments of the invention, there is a single location of motive force that is co-located with the target blister using a single reel design. In addition, assembly is easier, because a leader does not need to be threaded onto a spool (or multiple spools).

Referring again to FIG. 2, as the blister strip 202 progresses along the blister track 100, it eventually encounters junction 105 where it may proceed either along the continuous path 102 or the low-torque end path 104 as described above and shown in FIG. 1. Because the low-torque end path 104 is the path of least resistance for the blister strip 202 when the leading edge 208 is located at junction 105, the leading edge 208 enters the low-torque end path 104, subsequently resting in an intermediate position along the blister track 100 as shown in FIG. 2. Once it has entered the low-torque end path, the blister strip 202 continues advancing along this path until all medicament has been dispensed from the inhaler device, eventually arriving in the final position (FINAL), according to one embodiment.

Upon each engagement of the advancing mechanism by the engaging element, the blister strip 202 is moved by a distance along the blister track 100. In one embodiment, the distance may be predetermined such that it is sufficient to position a next blister in the withdrawing assembly 206. Of course, other distances are possible, such as variable distances according to blister placement, partial advancement of blisters, multiple blisters for each advancement, etc.

As is shown in FIG. 2, in some embodiments, the blister strip 202 is advanced through the blister track 100 using a single motive source, such as an advancing mechanism in one approach, that pulls the blister strip 202 such that unused blisters on the blister strip 202 are pulled to the withdrawing assembly 206 while used blisters on the blister strip 202 are pushed away from the withdrawing assembly 206.

The blister track 100 is configured such that the used blisters on the blister strip 202 are easily pushed along the blister track 100. More specifically, the blister return path uses one or more splines (which may be defined as variable radius curves in one approach) to ease movement of the blister strip 100 into and through the curvature changes of the splines. The curvature of the splines, in some embodiments, is kept constant at the transition points of the splines (which may be defined as an initial point of entry into the spline from a section of the blister track immediately preceding the spline), and then gradually gets tighter or looser to optimize the space available within the inhaler device. The shape of the return path is an important aspect of the inhaler device, in some approaches, because it allows for a consistently low torque profile across the range of movement of the blister strip 202 along the blister track 100.

Now referring to FIG. 3A, an image of an inhaler device with a separate end path loaded with a blister strip 202 in a final position is shown, according to one embodiment. As can be seen from this image, the leading edge 208 of the blister strip 202 may contact or come close to contacting the blister strip 202 at a point near an intersection of the secondary and the tertiary coil structures. FIG. 3B shows an engaging element and details of the withdrawing assembly, according to one embodiment. FIG. 3A also shows a portion of the advancing mechanism 220, according to one embodiment.

In some embodiments, a first blister 212 in the blister strip 202 may contain medicament, in which case the blister strip 202 may have a plurality of blisters 210, such as 31 blisters 210, one for each day of a 31-day month. In months that include less than 31 days, the inhaler device may be disposed of with blisters 210 remaining in a position prior to the withdrawing assembly 206 and/or unopened. When the first blister 212 does not contain medicament, there may be 32 blisters 210 present on the blister strip 202 to account for each day of a 31-day month, plus the blank first blister 212. It may be particularly advantageous to use an empty first blister 212 to verify expected operation of the inhaler device. For example, an empty first blister 212 may be utilized to test performance of the opening element, the dispensing element, the engaging element, and/or the advancing mechanism 220, along with positioning of the blister strip 202 within the inhaler device, in various approaches.

FIG. 3B shows a simplified schematic diagram of an inhaler device 300, according to one embodiment. As shown, the inhaler device 300 comprises a housing 302, a withdrawing assembly 206 disposed at least partially within the housing 302, the withdrawing assembly 206 being adapted for facilitating withdrawal of medicament from a target blister 320 of a blister strip 202 and conveying the medicament toward an exterior of the inhaler device 300. The withdrawing assembly 206 comprises an opening element 304 adapted for opening the target blister 320 of the blister strip 202 while the target blister 320 is positioned in the withdrawing assembly 206. The opening element 304 is operable by a user. The withdrawing assembly 206 also comprises a dispensing element 306 adapted for directing the withdrawn medicament toward the exterior of the inhaler device 300.

Furthermore, the inhaler device 300 also comprises a blister track 100 disposed within the housing 302, the blister track 100 being adapted for guiding each blister 210 of the blister strip 202 to the withdrawing assembly 206 in succession and storing the blister strip 202 prior to, during, and after use of blisters 210 of the blister strip 202. The blister track 100 may comprise the coil structures as previously described, according to one embodiment. In addition, the blister track 100 may comprise a low or very low friction material, such as polycarbonate (PC), acrylonitrile butadience styrene (ABS), polybutylene terephthalate (PBT), polyoxymethylene (POM) also referred to as acetal plastic, and other polymers as would be understood by one of skill in the art, in various embodiments. Of course, the blister track 100 may comprise other materials in combination with or without the plastic or polymer, such as metals, resins, and/or other suitable materials.

The inhaler device 300 also comprises the advancing mechanism 220 disposed within the housing 302, the advancing mechanism 220 being adapted for advancing the blister strip 202 by a predetermined distance each time the advancing mechanism 220 is engaged, and an engaging element 308 adapted for engaging the advancing mechanism 220 to advance the blister strip 202, the engaging element 308 being operable by the user.

For example, as can be seen in FIG. 3B, the inhaler device 300 includes the housing 302. The housing 302 may comprise a plastic or polymer material, such as polycarbonate (PC), acrylonitrile butadience styrene (ABS), polybutylene terephthalate (PBT), polyoxymethylene (POM) also referred to as acetal plastic, and other polymers as would be understood by one of skill in the art, in various embodiments. In particular, the housing 302 may comprise a material having a low or very low coefficient of friction. Of course, the housing 302 may comprise other materials in combination with or without the plastic or polymer, such as metals, resins, and other suitable materials. In FIG. 3B, the housing 302 appears only behind the components of the inhaler device 300 in order to illustrate the other components of the inhaler device 300, but in operation the housing 302 may include all the components of the inhaler device 300, in order to provide rigidity and protection to the inhaler device 300, among other functions. In some embodiments, the housing 302 may include only some of the components, while other components may be external of the housing 302, such as all or a portion of the dispensing element 306, in some approaches.

In some embodiments, the blister strip 202 may be discontinuous (e.g., not a loop, having a starting and ending portion) and may have a consistent pitch between centers of adjacent blisters 210, e.g., the distance between each blister 210 on the blister strip 202 is the same. In some embodiments, the consistent pitch between centers of adjacent blisters of the blister strip 202 may be less than about 12 mm, such as less than 11 mm, or less than 10 mm or less than 9 mm or less than 8 mm. Some pitch, is however, important, and may depend upon characteristics of the material used in the blister strip. Thus in some embodiments a pitch is between 5 and 10 mm, such as between 6 and 9 mm. In some embodiments, the pitch may be about 8 and 9 mm. In some embodiments, the blister strip 202 may comprise 32 blisters 210 comprising 31 blisters 210 having a medicament therein prior to withdrawal therefrom, and a first blister 212 having no medicament therein.

In some embodiments and as shown in FIGS. 3A and 3B, the advancing mechanism 220 may be a wheel structure with a plurality of grooves or notches defined by a plurality of teeth. Each tooth may be configured to accept a blister 210 of the blister strip 202. In operation, the blisters 210 arranged along the blister strip 202 fit into the grooves or notches. Furthermore, the advancing mechanism 220 drives the blister strip 202 along the blister track 100 by rotating in a clockwise direction (according to the perspective shown in FIG. 3B), thereby pushing the leading edge 208 of the blister strip 202 while pulling the trailing edge 209 of the blister strip 202 and requiring a relatively low amount of torque in order to operate. In some embodiments, the advancing mechanism 220 may comprise a track wheel positioned at a predetermined distance from the blister track 100 and adapted for advancing the blister strip 202 along the first radius of the primary coil structure, such as by a distance (in some embodiments equal to the pitch) between centers of adjacent blisters.

According to some embodiments, the inhaler device 300 may optionally include a counter mechanism (not shown) adapted for displaying a number of blisters 210 in the blister strip 202 which have been opened or have not been opened, e.g., the number of blisters 210 in the blister strip 202 remaining, or alternatively, the number of blisters 210 in the blister strip 202 that have been opened/used.

In some embodiments, the housing 302 may comprise two pieces of a structure coupled together, such as a clamshell configuration, molded plastic pieces, a top and bottom piece, etc., as would be understood by one of skill in the art upon reading the present descriptions. As shown in FIG. 3B, the housing 302 appears as a structure cut away above the shaded portion.

Referring again to FIG. 3B, in operation, the opening element 304 breaches one or more surfaces of the target blister 320 and establishes a connection between the target blister 320 and the dispensing element 306 via the withdrawing portion 206 of the inhaler device 300. Medicament contained within the target blister 320 may be conveyed from the target blister 320 toward the dispensing element 306 and subsequently toward the exterior of the inhaler device 300. In one particular embodiment, the opening element 304 may include a hollow piercing element adapted for piercing the target blister 320 and allowing withdrawal of medicament from the target blister 320 through the piercing element toward the dispensing element 306 and an operating element 322 adapted for causing the piercing element to engage the target blister 320 upon operation of the operating element 322.

In some embodiments, the dispensing element 306 may include one or more fluid configuration components, devices, elements or means to assist in enabling the patient's inspiratory efforts to evacuate and/or aerosolize the medicament withdrawn from the target blister 320. Such components, devices, elements or means act to direct, shape, alter, or enhance air flow and/or air pressure. In some embodiments, the fluid configuration components or means act to direct airflow at an angle to the blister surface of between about 0 and 90 degrees. In some embodiments the fluid configuration components or means may comprise a venturi tube. In some embodiments the fluid configuration components or means may comprise one or more vanes. In some embodiments, the dispensing element 306 may comprise a mouthpiece adapted for conveying the withdrawn medicament of the target blister 320 toward the user. Any mouthpiece may be used as known in the art, and the mouthpiece may be replaceable, removable, permanent, rigid, pliable, cleanable, etc., as would be understood by one of skill in the art. Moreover, the mouthpiece may include a plurality of outlets therein sufficient to direct the withdrawn medicament of the target blister 320 to the user upon inhalation by the user. In one such embodiment, two outlets may be provided within the mouthpiece.

In operation, a user interacts with the inhaler device 300 to receive a delivery of medicament. For example, in one embodiment, the user may operate the opening element 304 of the withdrawing assembly 206, which opens the target blister 320 positioned in the withdrawing assembly 206 and permits medicament to flow from the target blister 320 to the dispensing element 306 within the withdrawing assembly 206 and subsequently to the user. After receiving medicament, the user operates the engaging element 308, which may comprise a moveable cap 324 adapted for covering the mouthpiece in one embodiment. Upon user operation, the engaging element 308 engages the advancing mechanism 220 in order to advance the blister strip 202 by a predetermined distance each time the advancing mechanism 220 is engaged. Subsequent doses of medicament may be accessed by repeating this process until all medicament has been dispensed from the inhaler device 300, e.g., the blister strip 202 has been moved from initial position to final position.

The moveable cap 324 and housing 302 as shown in FIG. 3B are transparent in order to visualize the components contained therein and/or behind. Of course, in practice the inhaler device 300 may utilize a moveable cap 324 and/or housing 302 of any degree of transparency or opacity. In various embodiments, the moveable cap 324 and the opening element 304 may be interlocked such that the moveable cap 324 engages the advancing mechanism 220 when the moveable cap 324 is transitioned from an open position to a closed position only after the opening element 304 has been operated. That is to say, the engaging element 308 only engages and operates the advancing mechanism 220 after medicament has been dispersed from the inhaler device 300 and/or the target blister 320 has been opened by the opening element 304.

According to some embodiments, the inhaler device 300 may have overall dimensions of less than about 12.0 cm by about 7.5 cm by about 3.5 cm. For example, as shown in FIG. 3B, a width D3 of the inhaler device 300 may be less than about 7.5 cm, such as about 5.5 cm, in one approach. Furthermore, a length D4 of the inhaler device 300 may be less than about 12.0 cm, such as about 11.5 cm, in one approach. Although not shown in FIG. 3B, a depth (into the page) of the inhaler device 300 may be less than about 3.5 cm, such as about 3.0 cm in one approach.

Referring now to FIG. 3C, the primary coil structure 108, the secondary coil structure 110 and the tertiary coil structure 112 are shown on exemplary schematics of inhaler device blister tracks 100, according to one embodiment. As shown in FIG. 3C, the coil structure is illustrated as a heavier line overlaid upon the blister track 100. It should be noted that some portions of the blister track 100 may be shared by one or more coil structures, in various embodiments. Of course, as would be understood by one having ordinary skill in the art and as described previously, the blister track 100 may include additional and/or alternative coil structures without departing from the subject matter of the present invention. As previously indicated, there may be a different number of coil structures (more or less) and/or the coil structures may have different shapes, overlapping portions, configurations, etc., as would be understood by one of skill in the art upon reading the present description.

Figure 4A:
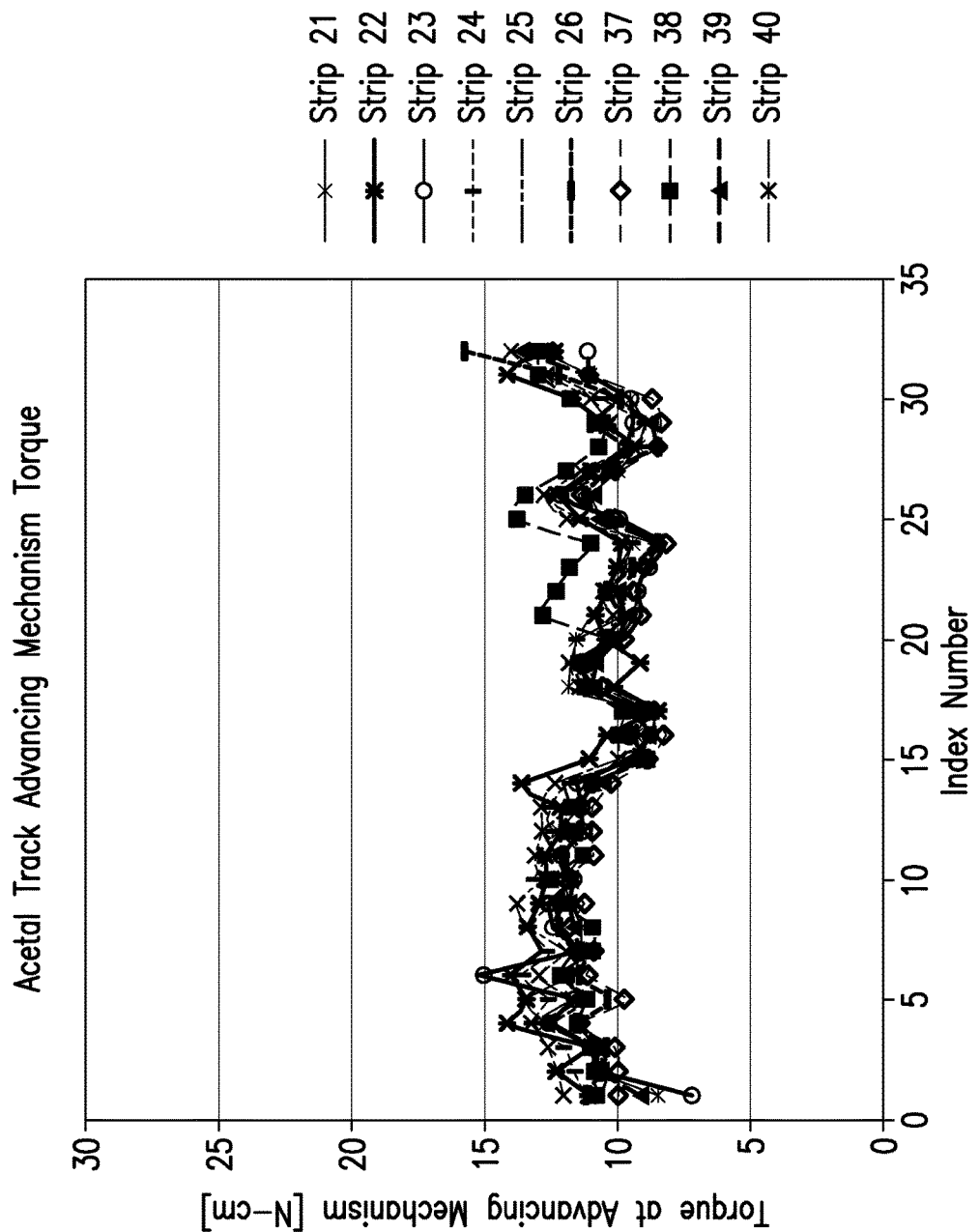
FIG. 4A is a graphical representation of index wheel torque observed over the lifetime of an acetal-polymer inhaler device, according to one embodiment.
Figure 4B:
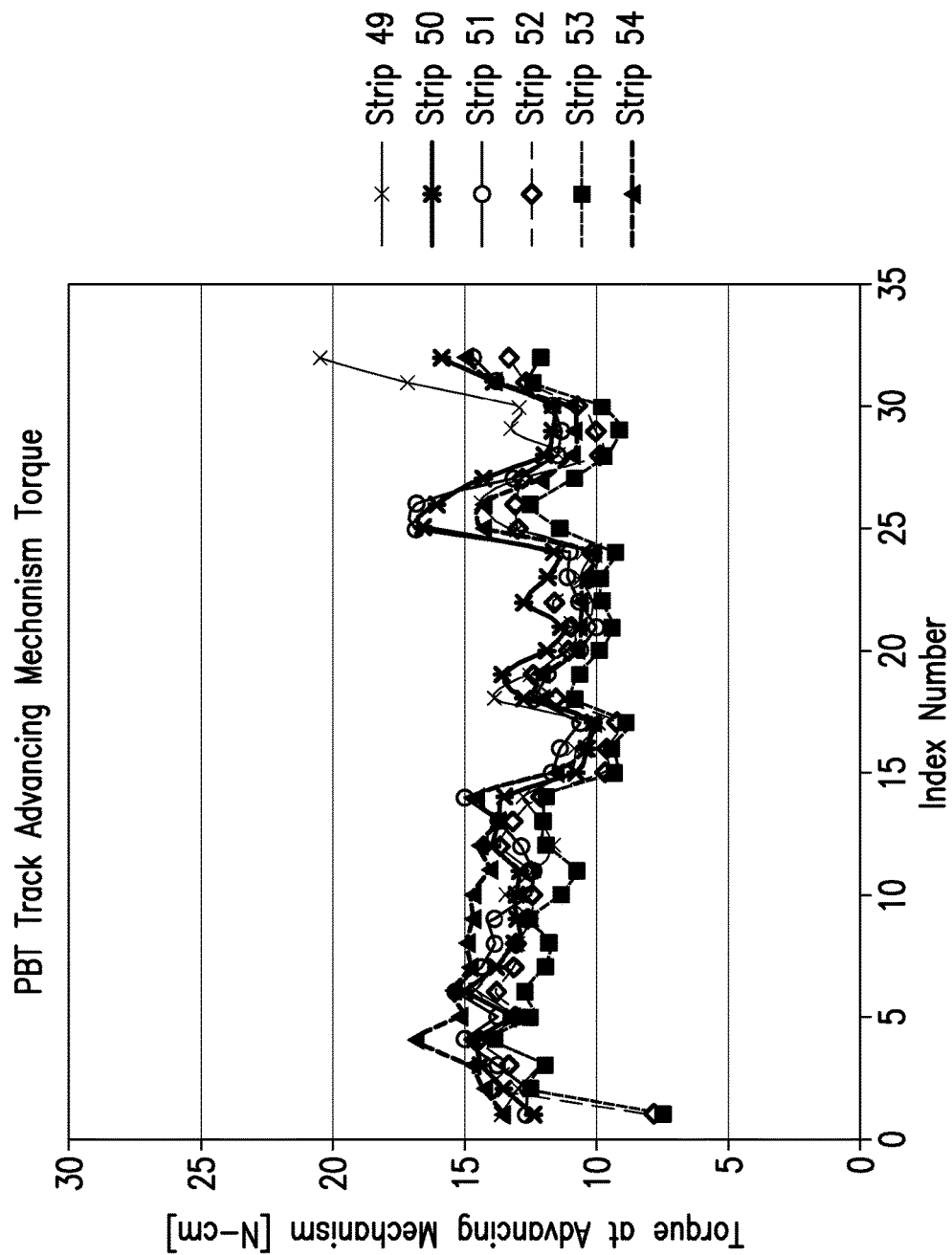
FIG. 4B is a graphical representation of index wheel torque observed over the lifetime of a PBT-polymer inhaler device, according to one embodiment.

Referring now to FIGS. 4A and 4B, graphical representations of data are presented and show the torque required to advance the blister strip along the blister track using the advancement mechanism over the life of several exemplary embodiments of the inhaler device.

FIG. 4A shows data for the torque experienced over the life of an inhaler device as described herein using a blister track comprising acetal copolymer. The y-axis represents the torque required to advance the blister along the blister track, measured at the advancement mechanism, and the x-axis indicates the blister position, or index number, present in the withdrawing assembly of the inhaler device requiring the torque to advance to the next position. Each of the curves represents an entire blister strip passing through the device via the blister track, and generally indicate that the torque required to advance the blister strip remains relatively constant in a range from about 7.5 Newton centimeters (N·cm) to about 15 N·cm, with two advancements out of about 320 (10 blister strips) requiring a maximum torque of about 16 N·cm, according to various embodiments using a blister strip.

FIG. 4B shows data for the torque experienced over the life of an inhaler device as described herein using a blister track comprising PBT. As in FIG. 4A, the y-axis represents the torque required to advance the blister along the blister track, measured at the advancement mechanism, and the x-axis indicates the blister position, or index number, present in the withdrawing assembly of the inhaler device requiring the torque to advance to the next position. In FIG. 4B, each of the curves represents an entire blister strip passing through the device via the blister track, and generally indicate that the torque required to advance the blister strip remains relatively constant in a range from about 7.5 N·cm to about 17.5 N·cm, with two advancements out of 192 (6 blister strips) requiring a maximum torque of about 21 N·cm, according to various embodiments using a blister strip comprising PBT.

Accordingly, in some embodiments a torque required to advance the blister strip is between about 6 and 20 N·cm, such as between about 6 and 18 N·cm, or between about 7 and 15 N·cm. In some embodiments, a torque required to advance the blister strip varies from a first blister to a last blister by no more than about 25%, such as no more than about 20% or 18% or 15% or 10%.

Referring now to FIG. 5, a graphical comparison of torque required to advance a blister strip along a prior art continuous loop blister track comprising acetal copolymer versus torque required to advance a blister strip along a discontinuous blister track comprising PBT is shown, according to one embodiment. As can be seen from FIG. 5, the torque required to advance the blister strip along the discontinuous track is more stable (less variable) and lower than the torque required to advance the blister strip along the prior art continuous loop blister track, especially in later advancements of blisters 21-32. Accordingly, the discontinuous blister strip and blister track of the inhaler device described herein according to various embodiments represents an improvement in the stability and overall reduction in the amount of torque required to advance a blister strip along a blister track in an inhaler device.

Figure 6:
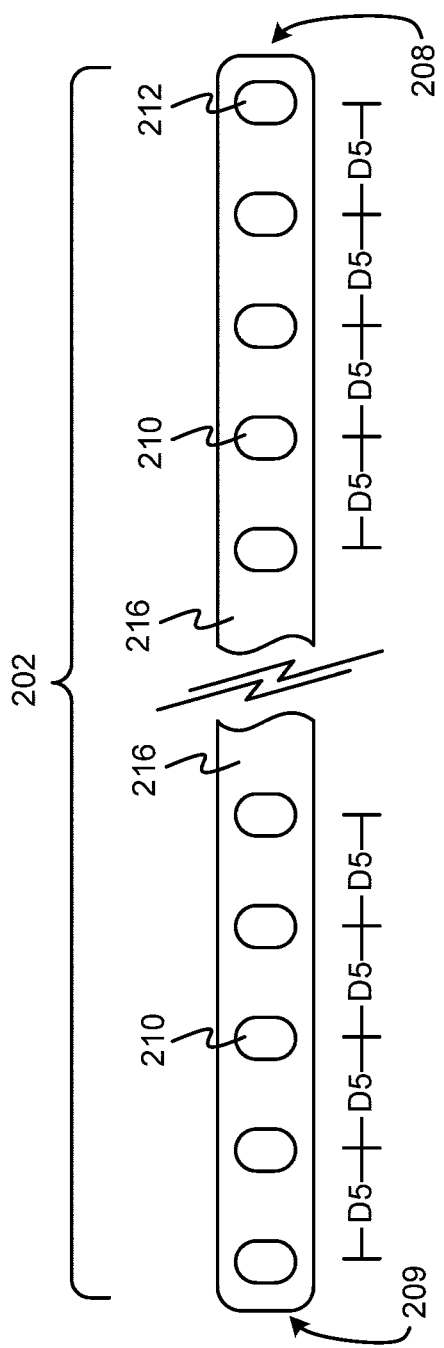
FIG. 6 is a schematic of a blister strip, according to one embodiment.

According to one embodiment, and as shown particularly in FIG. 6, the exemplary blister strip 202 may include up to 31 active doses of a medicament, which may be contained within blisters 210 arranged on a strip 216, which may comprise any suitable material, such as foil, metal polymer, flexible material, etc. In one embodiment, the blister strip 202 may comprise fillets (particularly at the leading edge 208), which may reduce the torque necessary to advance the blister strip 202 through the blister track. In some embodiments, an additional first blister 212 may be included nearest the leading edge 208 of the strip 216 for a total of 32 blisters per discontinuous blister strip. In particular, the additional blister 212 may be useful in operational testing of the inhaler device, for example to test the operation of the blister strip advancement mechanism, the blister opening mechanism, the medicament delivery mechanism, etc., as would be understood by one having ordinary skill in the art upon reading the present descriptions.

As shown in FIG. 6, each of the blisters 210 arranged along the strip 216 are separated by a uniform distance D5 as measured from center-to-center of adjacent blisters 210. In some embodiments, the blisters may be separated by a distance D5 of between about 7 mm and 9 mm, such as about 8 mm.

The intended use of the discontinuous blister track is to guide the blister strip throughout the inhaler use life with a minimum blister advance torque mean, maximum, and variability, while also minimizing the track size.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. An inhaler device comprising:
   a housing;
   a withdrawing assembly disposed at least partially within the housing, the withdrawing assembly being adapted for facilitating withdrawal of medicament from a target blister of a blister strip and conveying the medicament toward an exterior of the inhaler device, wherein the withdrawing assembly comprises an opening element comprising a hollow piercing element adapted for opening by piercing the target blister of a discontinuous blister strip while the target blister is positioned in the withdrawing assembly, wherein the opening element is operable by a user, the opening element further comprising an operating element adapted for causing the piercing element to pierce the target blister upon operation of the operating element;
   a dispensing element adapted for directing the withdrawn medicament toward the exterior of the inhaler device;
   a blister track disposed within the housing, the blister track being adapted for guiding each blister of the blister strip to the withdrawing assembly in succession and storing the blister strip prior to, during, and after use of blisters of the blister strip, wherein the blister track comprises:
      a primary coil structure comprising a first radius;
      a secondary coil structure comprising a second radius, a third radius, and a fifth radius;
      a tertiary coil structure comprising a second radius, a fourth radius, and a fifth radius, wherein third radius, the fourth radius and the fifth radius have coinciding center points;
      wherein the blister track comprises a feeding path adapted for storing the blister strip prior to blisters of the blister strip passing through the withdrawing assembly and a return path adapted for storing the blister strip after blisters of the blister strip have passed through the withdrawing assembly, wherein a portion of the feeding path is shared by a portion of the return path and a portion of the feeding path is different than a portion of the return path;
   an advancing mechanism disposed within the housing, the advancing mechanism being adapted for advancing the blister strip by a predetermined distance each time the advancing mechanism is engaged, wherein the advancing mechanism pulls blisters of the blister strip from the feeding path of the blister track; and
   an engaging element adapted for engaging the advancing mechanism to advance the blister strip, the engaging element being operable by the user.

2. The inhaler device as recited in claim 1, wherein the advancing mechanism comprises a track wheel positioned at a predetermined distance from the blister track and adapted for advancing the blister strip along the first radius of the primary coil structure.

3. The inhaler device as recited in claim 1, wherein the dispensing element comprises at least one fluid configuration component adapted for conveying the withdrawn medicament of the target blister toward the user.

4. The inhaler device as recited in claim 1, wherein the engaging element comprises a moveable cap adapted for covering a mouthpiece, and wherein the engaging element and the opening element are interlocked such that the engaging element engages the advancing mechanism when the moveable cap is transitioned form an open position to a closed position only after the opening element has been operated.

5. The inhaler device as recited in claim 1 wherein the path of the blister track is configured for providing a resistance of within about ±20% of a resistance value regardless of the position of a blister strip in the blister track as the blister moves therethrough.

6. The inhaler device as recited in claim 1, wherein an amount of resistance to operation of the engaging element for advancing the blister strip past a first blister is about equal to an amount of resistance to operation of the engaging element for advancing the blister strip past a final blister.

7. The inhaler device as recited in claim 6, wherein the blister track is configured to allow for a consistent torque profile while the advancing mechanism pulls blisters of the blister strip from the feeding path and pushes blisters of the blister strip toward the return path.

8. The inhaler device as recited in claim 1, wherein the return path comprises one or more splines comprising variable radius curves adapted for easing movement of the blister strip into and through curvature changes of the one or more splines, wherein the curvature of each of the one or more splines is constant at a transition point and gradually tightens or loosens after the transition point.

9. The inhaler device as recited in claim 8, wherein the fifth radius is greater than the first radius, wherein the first radius is greater than the fourth radius, wherein the fourth radius is greater than the third radius, and wherein the third radius is greater than the second radius.

* * * * *